(12) United States Patent  (10) Patent No.:     US 7,144,550 B2
Devine et al.                    (45) Date of Patent:         Dec. 5, 2006

(54) MOBILE APPARATUS AND PROCESS FOR TREATING INFECTIOUS WASTE

(75) Inventors: Thomas J. Devine, Houston, TX (US); Bobby Clark, Houston, TX (US)

(73) Assignee: T & C Devine, Ltd., Houston, TX (US)

( * ) Notice: Subject to any disclaimer, the term of this patent is extended or adjusted under 35 U.S.C. 154(b) by 43 days.

(21) Appl. No.: 10/754,146

(22) Filed: Jan. 9, 2004

(65) Prior Publication Data

US 2004/0141877 A1    Jul. 22, 2004

Related U.S. Application Data

(60) Provisional application No. 60/438,922, filed on Jan. 9, 2003.

(51) Int. Cl.
   *A61I 2/16*    (2006.01)
(52) U.S. Cl. ..................... 422/28; 422/37; 422/300; 241/21; 241/41; 241/60; 241/101.01; 241/606; 241/DIG. 38
(58) Field of Classification Search ................. 422/28, 422/37, 292, 300; 241/21, 41, 60, 101.01, 241/606, DIG. 38
   See application file for complete search history.

(56) References Cited

U.S. PATENT DOCUMENTS

| 4,578,185 | A | * | 3/1986 | Wilson et al. ............... 210/85 |
| 4,884,756 | A | * | 12/1989 | Pearson ....................... 241/42 |
| 5,213,774 | A | * | 5/1993 | Noetzel ...................... 422/292 |
| 5,364,589 | A | * | 11/1994 | Buehler et al. .............. 422/26 |
| 5,698,095 | A | * | 12/1997 | Kami .......................... 210/173 |
| 5,720,438 | A | * | 2/1998 | Devine et al. ............... 241/21 |
| 5,941,468 | A | * | 8/1999 | Lewis et al. ................. 241/17 |
| 6,536,133 | B1 | * | 3/2003 | Snaper ........................ 34/265 |
| 2001/0016181 | A1 | * | 8/2001 | Benson ....................... 422/295 |

* cited by examiner

*Primary Examiner*—E. Leigh McKane
(74) *Attorney, Agent, or Firm*—Kenneth A. Roddy

(57) ABSTRACT

A mobile self-contained apparatus and process for grinding, grating, macerating, chemically disinfecting, and drying infectious waste material. A trailer (10) contains a hopper (27), a grinder/grater (28), an enclosed conveyor system, drying and filter apparatus, and sources of power, chemical disinfectant, and fresh water. Bagged infectious waste material in a cart is lifted and dumped into the hopper, sprayed with a sodium hypochlorite disinfectant solution, fed to the grinder/grater, ground, grated, and macerated into small particles of confetti-like material, sprayed again, immersed in the disinfectant solution, conveyed by an upwardly inclined screw conveyor (34) and thoroughly mixed therein, dried, passed into a vertical screw conveyor (47), and passed to a discharge screw conveyor (50) which discharges the dry confetti-like material. The enclosed system operates under negative pressure produced by a suction fan that draws the air within the system through a HEPA filter to remove chemical fumes, airborne dust, odors and bacteria.

11 Claims, 4 Drawing Sheets

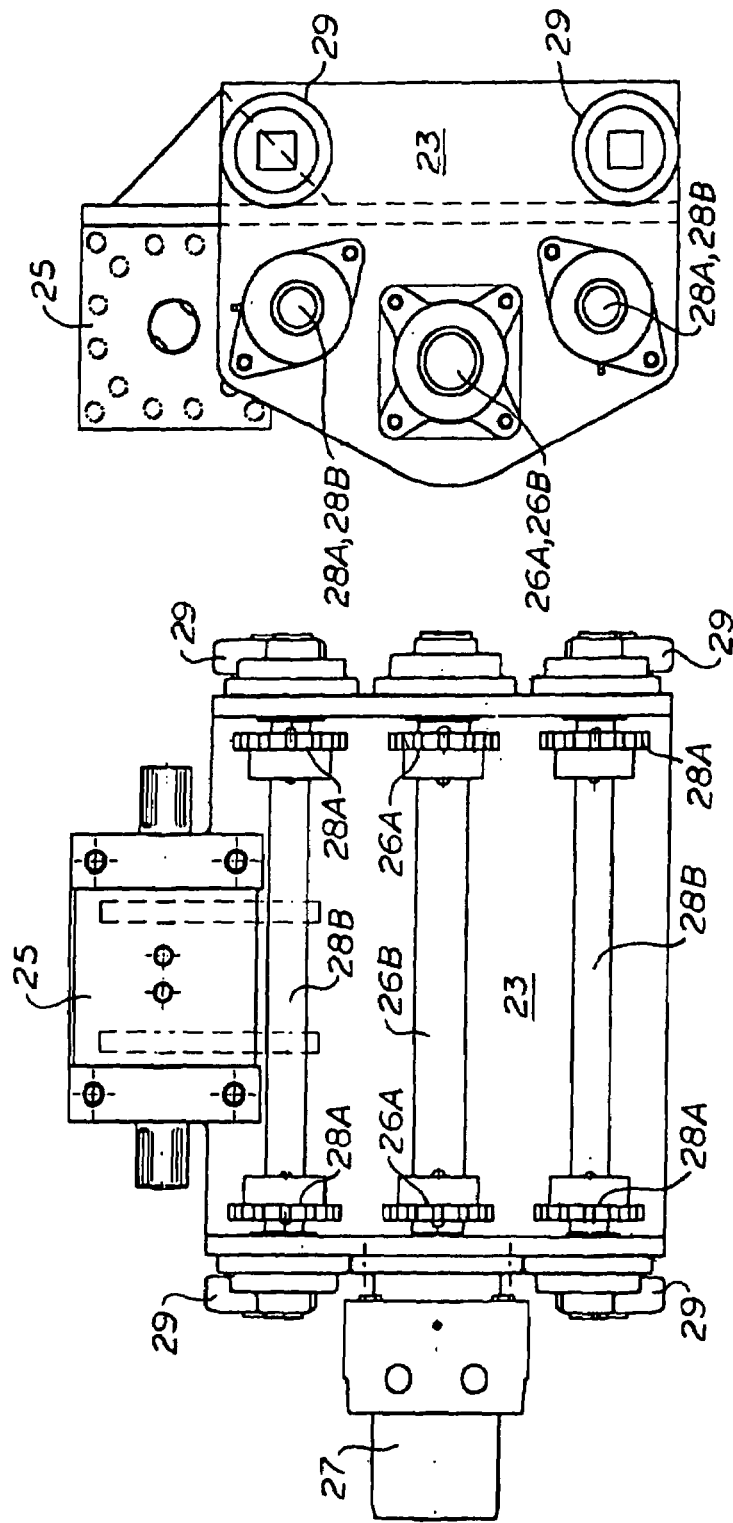

MOBILE APPARATUS AND PROCESS FOR TREATING INFECTIOUS WASTE

CROSS REFERENCE TO RELATED APPLICATION

This application claims priority of U.S. Provisional Application Ser. No. 60/438,922, filed Jan. 9, 2003.

BACKGROUND OF THE INVENTION

1. Field of the Invention

This invention relates generally to waste material treatment apparatus and processes, and more particularly to a self contained mobile apparatus and improved process for grinding, grating, macerating, chemically disinfecting, and drying medical waste materials on-site at health care related facilities.

2. Brief Description of the Prior Art

The following terms, as used herein, are recognized in government regulations, and in the trade, as distinguishing one type of medical waste treatment process from another. "STERILIZATION" is a process that destroys all microbial life including large numbers of bacterial endospores. "DISINFECTION" is a somewhat less lethal process than sterilization, which destroys or inactivates viruses, fungi, and bacteria (but not necessarily their endospores) on inanimate surfaces. "CHEMICAL DISINFECTION" is the use of a chemical agent to reduce significantly the numbers of active microorganisms (but not necessarily their endospores) from the surfaces of inanimate objects. "INCINERATION" is the process of burning waste in an incinerator. "AUTOCLAVING" is the process wherein waste material is sterilized with steam in an enclosed compartment. "UNRECOGNIZABLE" means that the original appearance of the waste item has been altered such that neither the waste nor its source can be identified. "GRINDING" is the physical process which pulverizes materials, thereby rendering them as unrecognizable, and for sharps, reduces the potential for the material to cause injuries such as puncture wounds. "SHREDDING" is the physical process which cuts, slices, or tears materials into small pieces. "CHLORINE DISINFECTION/MACERATION" is the process of shredding waste in the presence of a chlorine solution under negative pressure.

The description of infectious medical waste and the approved methods of handling this waste vary from state to state. Generally, infectious medical waste, or "red bag" waste is defined as including body fluids, microbiological waste, pathological waste, sharps, and animal waste. The term "red bag" is the red bag that hospitals are required by government regulations to use for containing infectious medical waste to clearly identify the contents. Red bag waste does not include radioactive materials, large quantities of chemicals, or large metal objects. A "$\log_{10}$ reduction" is a mathematically defined unit used in reference to level or degree of microbial inactivation. A 4 $\log_{10}$ reduction represents a 99.99% reduction in the numbers of active microorganisms, while a 6 $\log_{10}$ reduction represents a 99.9999% reduction in the numbers of active microorganisms. A process to meet the criteria set out in regulatory guidelines for "on-site" processing of infectious medical waste requires that it be disinfected to guarantee a 4 $\log_{10}$ reduction or 99.99%, and must yield a product residue which is unrecognizable as to the source.

It is important to point out the basic microbiology and chemistry as it relates to "sterilization" and "disinfection".

As discussed above, "sterilization" destroys all microbial life including large numbers of bacterial endospores. On the other hand, "disinfectants", if properly used, will eliminate all pathogenic vegetative organisms but not all endospores. Since most endospore formers are non-pathogenic, an effective disinfectant will kill the broad range of potential pathogens. Hypochlorites (calcium and sodium) are relatively inexpensive, fast acting, and have a broad spectrum of anti-microbial activity. Their use as disinfectants is limited by their corrosiveness, inactivation by organic matter, and relative instability. The microbiocidal activity of chlorine is largely attributed to hypochlorous acid (HOCl). Hypochlorite ion (OCl) posses about $\frac{1}{80}$th the germicidal capacity of hypochlorous acid (HOCl). The chemical reaction which causes disassociation of hypochlorous acid (HOCl) to the less microbiocidal form hypochlorite ion (OCl), C12, and various sodium salts is dependent on pH. As the pH increases, more hypochlorite ion (OCl) is formed and the microbiocidal activity decreases. As the pH decreases, the concentration of hypochlorous acid (HOCl) increases and the microbiocidal activity increases. Hypochlorous acid (HOCl) is the "microbiocidal" component of the disassociated end products of sodium hypochlorite (NaOCl). The production of hypochlorous acid (HOCl) and resultant microbiocidal activity is at its greatest when the pH is in the range of from 4 to 6.

At a pH of 1.0 to 4.5, the reaction is driven to 90% to 95% C12. At a pH range of 4.5 to 6.0, the reaction is driven to 90% to 95% hypochlorous acid (HOCl). At a pH range greater than 6.0, the reaction is driven to 80% to 95% hypochlorite ion (OCl) and is less microbiocidal. If a sodium hypochlorite (NaOCl) disinfectant is adjusted to a pH of 4.0 to 6.0, the microbiocidal properties are enhanced to a factor of more than 100 times.

The present invention utilizes a sodium hypochlorite (NaOCl) solution adjusted to a pH of from about 4.0 to 6.0 to increase the hypochlorous acid (HOCl) component and significantly increase the microbiocidal activity of the disinfectant.

Traditionally, the majority of infectious medical waste has either been "incinerated" or "autoclaved" to render the end product non-infectious and unrecognizable. The residue of incineration has been deposited in landfills as fly ash or bottom ash. Incineration has become an unacceptable method due to recent air quality standards and problem areas concerning air emissions during incineration such as carcinogenic organic, dioxins, and furans, as well as acid gases. The controversy over incineration has resulted in substantial public opposition to the construction of new incinerators and frequent demonstrations demanding closure of existing incinerators.

"Autoclaving", wherein the bulk waste material is sterilized with steam in an enclosed compartment, also has many objectionable characteristics. Autoclaving alone does not change the physical appearance of the waste, resulting in uncertainty and fear among subsequent handlers. In many cases, autoclaved materials have been rejected at landfills. The cost of construction and operation precludes autoclaving as an acceptable alternative for treating large volumes of infectious medical waste. Other methods such as chemical disinfection, microwaving, thermal or dry heat inactivation, chlorine disinfection/maceration, and moist heat disinfection have been proposed. Most of these other methods either cannot meet the total volume requirements and/or do not significantly reduce the microbial colony count to acceptable levels.

Another major problem with prior art treatment methods is that the process is usually carried in large treatment plants which are built or fixed at a location remote from the waste generating facility, because of their requirements for large amounts of power, fluids, heat, and potential of fluid residue hazards.

Thus, another important objection to incineration, autoclaving, and other traditional methods of infectious waste treatment and disposal is the logistics of transporting the infectious medical waste material from the waste generating facility to the incinerator, autoclaving facility, microwaving facility, or chemical treatment plant over public thoroughfares and highways.

Federal regulations are very strict if infectious medical waste is taken away from the premises of the hospital or health care facility ("off-site") for incineration or other methods of disposal. The U.S. Department of Transportation has an entire set of regulations including special handling, recording, packaging, and storage, which must be followed by the health care facility, the hauler, and the receiver of the infectious waste. The health care facility must also have liability insurance, in the event of an accident before the waste materials are destroyed. However, if the waste materials are processed on the health care facility premises ("on-site"), there are substantially fewer requirements on the health care facility. Thus, the health care facility is faced with either transporting the infectious waste to a remote treatment plant or with a massive capital expenditure to build an on-site waste treatment system.

There are several patents which disclose various waste treatment apparatus and sterilization and disinfection processes, most of which require a large system of apparatus fixed-in-place on-site (not mobile) and require placement in close vicinity to sources of supply of power, fluids, and heat, or placement at a remote site which requires providing these sources of supply at the remote location. Thus, most of these systems require the health care facility to install the system on-site or to transport the waste to a remote location.

Swisher, Jr. et al, U.S. Pat. No. 6,446,887 discloses a portable medical waste plant for loading, reducing, and sterilizing medical waste. The system includes a frame supporting a generally sealed containment chamber, a lift assembly having a lifter mounted on a track assembly, a hopper mounted on the frame near the lift and in communication with a material feeder, a first grinder in communication with the material feeder, a first conveyor positioned to receive medical waste from the first grinder, and a second grinder in communication with the first conveyor. The system further includes a second conveyor positioned to receive waste from the second grinder, and an autoclave in the containment chamber in communication with the second conveyor assembly for thermally disinfecting the waste. The autoclave includes a plurality of steam inlets, a waste inlet opening, and a waste outlet opening for discharging waste to a third conveyor assembly. The third conveyor assembly is positioned to receive waste from the autoclave and to convey the waste to a disposal container. The system further includes a steam generation plant mounted on the frame in the containment chamber and in communication with the steam inlets of the autoclave.

Devine et al, U.S. Pat. No. 5,720,438, commonly owned with the present application, discloses a mobile self-contained apparatus and process for grinding, grating, macerating, chemically disinfecting, and drying infectious waste material on-site. A trailer contains a hopper, a first and second grinder/grater, four enclosed conveyors, drying and filter apparatus, and sources of power, chemical disinfectant, and fresh water. Bagged infectious waste material in a cart is lifted and dumped into a hopper, fed to a first grinder/grater, ground and grated into particles, immersed in a sodium hypochlorite (hypochlorous acid) chemical disinfectant solution, and conveyed by an enclosed upwardly inclined screw conveyor to a second grinder/grater. The particles are sprayed one or more times with the disinfectant and thoroughly mixed together as they are conveyed in the inclined conveyor and are dumped from the inclined conveyor into the second grinder/grater and further ground, grated, and macerated into smaller particles, and air dried to produce a dry confetti-like material which is unrecognizable as to the source. The confetti-like material is conveyed by an enclosed horizontal screw conveyor to an enclosed vertical screw conveyor where it is passed upwardly to an enclosed rotatable discharge screw conveyor which discharges the confetti-like material into a receptacle. The enclosed system operates under negative pressure produced by a suction fan which draws the air within the system through a HEPA filter to remove chemical fumes, airborne dust, odors and bacteria.

Devine et al, U.S. Pat. No. 5,720,438 is commonly owned with the present invention, and is hereby incorporated herein by reference. The present invention is an improvement over Devine et al, U.S. Pat. No. 5,720,438, in that the present invention not require a second grinder/grater, a second generator, or a horizontal conveyor between the inclined conveyor and the vertical conveyor. The modified grinder/grater of the present system also incorporates a slotted grid plate and cutter blade arrangement that effectively shreds and disintegrates the plastic material of the "red bag" that contains infectious medical waste and overcomes the problem of sticking and gumming caused by the bag material. The present system also incorporates a different disinfectant spraying arrangement that more efficiently disinfected the particles of waste. Thus, the present system is housed in a much small trailer chassis, is less expensive to manufacture and operate, and the process of treating infectious waste material is accomplished more efficiently, in fewer steps and in less time.

Kline et al, U.S. Pat. No. 5,656,248 discloses a multi-stage treatment system for infectious waste includes a shredding stage, a granulating stage, a wetting stage, a disinfecting stage, and a dewatering stage which define a continuous treatment flowpath for the infectious waste. A plurality of blades shred the waste in the shredding stage, then the waste is injected with volatile disinfectant chemicals which are mixed immediately before injection. A plurality of blades in a granulating stage then fragment the waste to a smaller particle size. The granulating stage insures that the waste is granulated to a sufficiently small size to facilitate the use of a relatively low concentration of a highly reactive disinfectant. Chemicals are mixed to form a volatile, highly reactive disinfectant which is then immediately injected into the waste downstream of the shredding stage. A plurality of jets wet the waste mixture in the wetting stage with the heated aqueous disinfectant. A flow restriction removes excess aqueous liquid from the disinfected waste in the dewatering stage and renders the product suitable for landfilling. A control system controls the temperature of the disinfectant to maintain an optimum temperature for a desired kill rate.

Kaneko, U.S. Pat. No. 5,397,535 discloses a process for converting various kinds of used and potentially infectious medical articles such as injection needles into an aggregate for construction materials such as concrete. The articles are first crushed into pieces to such an extent that the shape of the articles cannot be visually identified. Subsequently, the crushed medical articles and particulate absorbent are introduced into a mixer and mixed and heated therein to a temperature above 180° C. by use of a heater in combination with frictional heat generated as the mixer blade is rotated, whereby the crushed infectious medical waste articles are completely sterilized. The particulate absorbent serves to absorb any unpleasant odor or toxic gas which is generated from the crushed infectious medical articles during heating.

Miller et al, U.S. Pat. No. 5,346,142 discloses a fixed-in-place apparatus and method for shredding and sterilizing medical waste material wherein the waste material is initially shredded by a primary shredder, sprayed with a sterilant and mixed in a screw conveyor, fed into a second higher speed shredder for further shredding, fed into a second screw conveyor for further mixing, fed into a turbo blender which further mixes and shatters any substantially sized particles remaining after shredding and moves it into a conveyor, and it is finally discharged as unrecognizable waste material. The disclosure is silent as to the type of sterilant used.

Goldner et al, U.S. Pat. No. 5,270,000 discloses an apparatus and process for treating medical hazardous wastes to process them into waste similar to domestic refuse which can be removed or disposed of like normal domestic refuse or can be supplied for recycling after sorting. The infectious refuse is passed through a microwave chamber fitted with a plurality of microwave sources disposed next to each other and subjected to disinfection therein. The apparatus has a two-stage construction of microwave chamber and temperature maintenance chamber. The microwave chamber has a dense microwave field distribution for heating the refuse to or above a selectable minimum temperature. The temperature maintenance chamber connected to the outlet of the microwave chamber holds the refuse at least the minimum temperature during a minimum residence time.

Noetzel, U.S. Pat. No. 5,213,774 discloses a mobile disinfection apparatus for hospital waste that has a worm conveyor leading from the bottom of the charging shaft at the back of a trailer bed to the mouth of a rotary tube reactor or rotary kiln enclosed in a heated hood which can be subdivided into separately heated zones. The reactor is formed with scoops which lift the waste comminuted in the charging shaft and cause it to cascade to contact the sterilizing medium and the sterilized waste passes into a discharge housing in which the waste is separated from the sterilizing medium which is recycled. The waste can be discharged and compacted by a worm conveyor which can be swung laterally outwardly from its transport position to discharge the waste for further handling like household or municipal waste.

Pearson, U.S. Pat. Nos. 5,173,257 and 5,116,574 disclose a fixed-in-place chemical disinfection process and apparatus for the treatment of infectious medical waste utilizing ozone wherein the medical waste is subjected to an ozone liquid or gas disinfectant, shredded, fed to a separation tank, fed to from 1 to 6 reactor vessels where ozone gas bubbles pass through the infectious waste material. The ozone disinfection process requires contacting times of from about 5 to about 45 minutes to effectively disinfect the waste.

Pearson, U.S. Pat. Nos. 5,077,007 and 5,078,965 disclose a fixed-in-place chemical disinfection process and apparatus for the treatment of infectious medical waste utilizing ozone wherein the medical waste is subjected to an ozone liquid or gas disinfectant, shredded, fed to a separation tank, fed to a fluidized bed reactor vessel where ozone gas bubbles pass through the infectious waste material. The ozone disinfection process requires contacting times of from about 5 to about 45 minutes to effectively disinfect the waste.

Mennel et al, U.S. Pat. No. 5,054,696 discloses a fixed-in-place medical waste disposal system for disposing of biologically contaminated waste situated inside a rigid, form-stable container which includes a screw auger which shreds the material and may mix the shredded mass with a liquid disinfectant solution. The auger transports the mass to a hammermill which disintegrates the shredded mass into an unrecognizable particulate. The disclosure is silent as to the type of disinfectant fluid used.

Pearson, U.S. Pat. No. 4,884,756 discloses a fixed-in-place infectious waste treatment system wherein the waste is placed into a feeding channel and moved by a ram into a series of shredders and is then gravity fed into a disinfecting fluid contained within an enclosed decontamination and separation device. The disclosure is silent as to the type of disinfectant fluid used or whether the material is discharged in a soaked condition.

Wilson et al, U.S. Pat. No. 4,618,103 discloses a relatively small hospital waste disposal system wherein a hammermill, a disinfectant solution, and separator tank divided into collecting pools which are adapted for connection to a sewer for disposing of the disinfectant are contained in a sealed cabinet which is placed in patient wards of a hospital. The disclosure is silent as to the type of disinfectant solution used.

Wilson et al, U.S. Pat. No. 4,578,185 discloses a fixed-in-place hospital waste disposal system wherein an inclined belt conveyor transfers waste materials through slitted curtains and drops it into a shredder while it is sprayed with a sodium hypochlorite solution having a pH of 8.5 and then enters a hammermill. The particles are then fed through a particle separator where solid particles are separated from the liquid disinfectant for independent evacuation. The liquids are evacuated to the sewer system and the solids are deposited in a cart. The system also includes vacuum ventilation elements to maintain any released bacteria or particles in the system until completely processed. As pointed out above, when the pH range of sodium hypochlorite is greater than 6.0, the reaction is driven to 80% to 95% hypochlorite ion (OCl) and is less microbiocidal than a solution with a pH of 6.0 or less.

Lovercheck, U.S. Pat. No. 3,547,577 discloses a wheeled vehicle for processing and sterilizing refuse such as trash and domestic garbage which carries a shredding machine that shreds the garbage which is then heated by a heater, a compactor which compresses the shredded material into briquettes, and a tank wherein the briquettes are contacted with a microbiocidal gas such as ethyelene oxide, propylene oxide, methyl bromide, or betapropiolactone.

The present invention overcomes the problems discussed above and provides a very cost effective alternative to transporting infectious waste and building new on-site waste treatment systems for each health care facility.

The present invention is distinguished over the prior art in general, and these patents in particular by a mobile self-contained apparatus and process for grinding, grating, macerating, chemically disinfecting, and drying infectious waste material on-site. A trailer contains a hopper, a grinder/grater, enclosed conveyors, drying and filter apparatus, and sources of power, chemical disinfectant, and fresh water. Bagged infectious waste material in a cart is lifted and dumped into a hopper, sprayed with a sodium hypochlorite (hypochlorous acid) chemical disinfectant solution, fed to a grinder/grater, ground, grated, and macerated into small particles, sprayed again and immersed in the chemical disinfectant solution, and conveyed by an enclosed upwardly inclined screw conveyor where they are thoroughly mixed together, and dried to produce a dry confetti-like material which is unrecognizable as to the source. The confetti-like material is discharged into an enclosed vertical screw conveyor where it is passed upwardly to an enclosed rotatable discharge screw conveyor that discharges the confetti-like material into a receptacle. The enclosed system operates under negative pressure produced by a suction fan that draws the air within the system through a HEPA filter to remove chemical fumes, airborne dust, odors and bacteria.

SUMMARY OF THE INVENTION

It is therefore an object of the present invention to provide a mobile self-contained apparatus and process for grinding, grating, macerating, chemically disinfecting, and drying infectious waste material.

It is another object of this invention to provide a mobile self-contained apparatus and process for grinding, grating, macerating, chemically disinfecting, and drying infectious waste material which is a very cost effective alternative to transporting infectious waste and building new on-site waste treatment systems for individual health care facilities.

Another object of this invention is to provide a mobile self-contained apparatus and process for on-site grinding, grating, macerating, chemically disinfecting, and drying infectious waste material which eliminates the potential hazards of transporting untreated infectious waste material from the waste generating facility to a remote treatment plant over public thoroughfares and highways.

Another object of this invention is to provide a mobile self-contained apparatus and process for grinding, grating, macerating, chemically disinfecting, and drying infectious waste material which renders it into a substantially dry confetti-like material unrecognizable as to its source which can then be safely transported to a landfill along with general waste from the health care facility.

Another object of this invention is to provide a mobile self-contained apparatus and process for grinding, grating, macerating, chemically disinfecting, and drying infectious waste material which utilizes a sodium hypochlorite (NaOCl) disinfectant solution adjusted to a pH of about 4.0 to about 6.0 and final concentration of 2,500 ppm hypochlorous acid and will consistantly produce at least a 4 $\log_{10}$ reduction or 99.99%, and in most cases, a 6 $\log_{10}$ reduction or 99.9999% reduction in the numbers of active microorganisms.

Another object of this invention is to provide a mobile self-contained apparatus and process for grinding, grating, macerating, chemically disinfecting, and drying infectious waste material which can process from 1,500 to 3,000 pounds of waste per hour.

A further object of this invention is to provide a mobile self-contained apparatus and process for grinding, grating, macerating, chemically disinfecting, and drying infectious waste material which is economical to manufacture and operate and does not require outside sources of power, fluids, or heat.

A still further object of this invention is to provide a mobile self-contained apparatus and process for grinding, grating, macerating, chemically disinfecting, and drying infectious waste material which is quiet in operation, non-polluting, and does not require the assistance of any medical personnel.

Other objects of the invention will become apparent from time to time throughout the specification and claims as hereinafter related.

The above noted objects and other objects of the invention are accomplished by a mobile self-contained apparatus and process for grinding, grating, macerating, chemically disinfecting, and drying infectious waste material on-site. A trailer contains a hopper, a grinder/grater, enclosed conveyors, drying and filter apparatus, and sources of power, chemical disinfectant, and fresh water. Bagged infectious waste material in a cart is lifted and dumped into a hopper, sprayed with a sodium hypochlorite (hypochlorous acid) chemical disinfectant solution, fed to a grinder/grater, ground, grated, and macerated into small particles, sprayed again and immersed in the chemical disinfectant solution, and conveyed by an enclosed upwardly inclined screw conveyor where they are thoroughly mixed together, and dried to produce a dry confetti-like material which is unrecognizable as to the source. The confetti-like material is discharged into an enclosed vertical screw conveyor where it is passed upwardly to an enclosed rotatable discharge screw conveyor that discharges the confetti-like material into a receptacle. The enclosed system operates under negative pressure produced by a suction fan that draws the air within the system through a HEPA filter to remove chemical fumes, airborne dust, odors and bacteria.

BRIEF DESCRIPTION OF THE DRAWINGS

FIGS. 2 and 3 are a side and a front elevation view, respectively, of the lift carriage assembly of the hydraulic lift.

DESCRIPTION OF THE PREFERRED EMBODIMENTS

Figure 1:
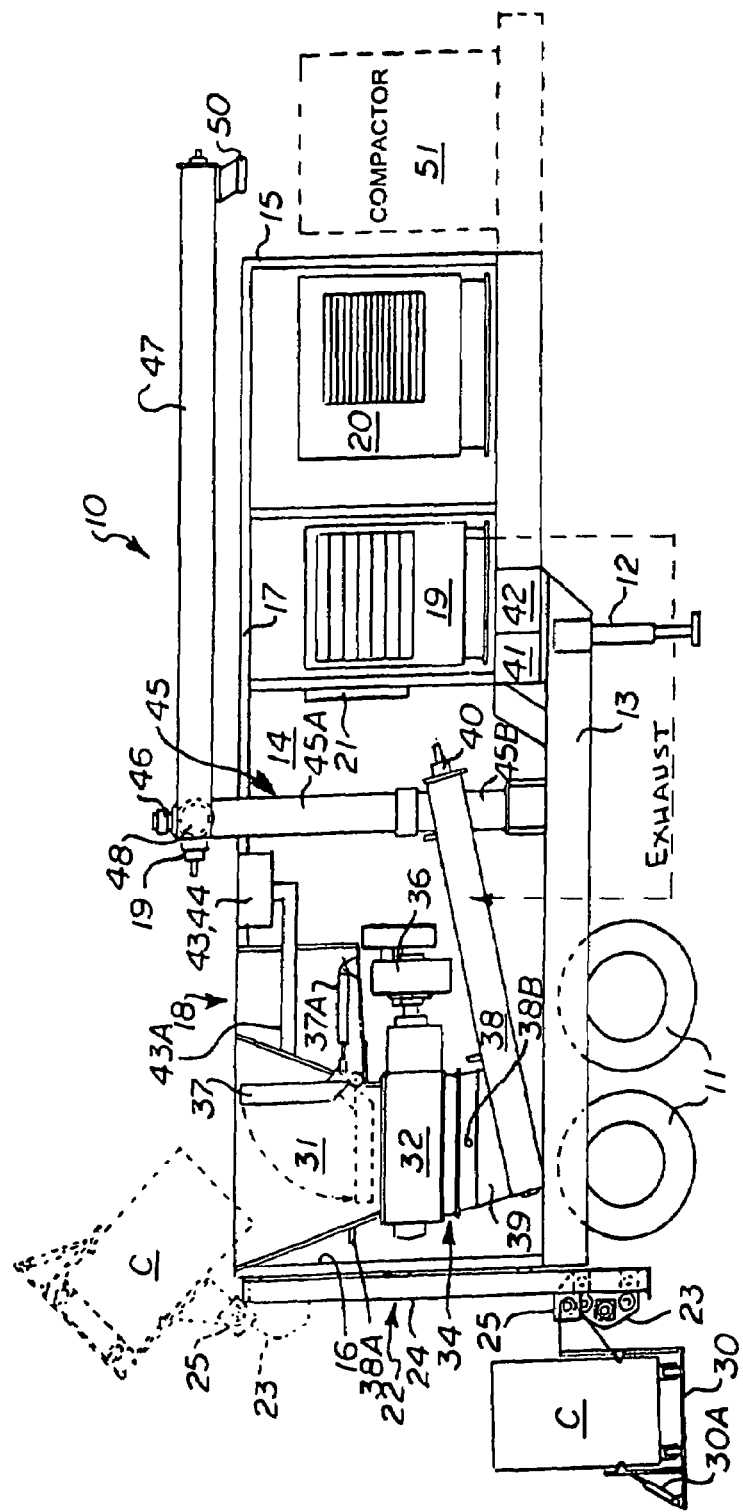
FIG. 1 is a schematic side elevation of the mobile waste processing trailer which contains apparatus for processing waste materials in accordance with the present invention.

Referring to the drawings by numerals of reference, there is shown in FIG. 1, a mobile waste processing trailer 10 which contains a system of apparatus 18 for processing waste materials. The waste processing apparatus 18 is contained substantially within the enclosed wheeled trailer 10 which may be coupled to a truck tractor and transported to various job sites and health care related facilities such as hospitals, clinics, doctor's offices, etc., for processing waste materials, such as infectious medical waste material on-site. The trailer 10 has an elongated frame supported at the rear end by rear wheels 11 and at a forward end by extensible legs or jacks 12.

The trailer 10 has a floor or bottom wall 13, opposed side walls 14, front and rear walls 15 and 16, respectively, and a top wall 17 which surround and enclosure the waste processing apparatus 18 mounted inside with the exception of a discharge screw conveyor 47 which is disposed exterior of the trailer enclosure. The walls of the trailer 10 are formed of a suitable material and may be provided with suitable seals to form a secondary enclosure for containing spills and gases in the event of accidental leakage from the components inside. The walls of the trailer may also be insulated to control temperature and noise. As explained hereinafter, the discharge screw conveyor 47 can rotate 360° about a vertical axis and relative to the trailer to facilitate discharging the processed waste material into a convenient receptacle, such as a dumpster, compactor, or dump truck.

In a preferred embodiment the trailer 10 is approximately 24 feet in length including a hydraulic lift mechanism mounted on the rear end of the trailer (described below). The trailer and apparatus of the present invention may also be provided in the form of a garbage truck, a stationary skid mounted unit, and small easily transportable trailer units.

A diesel driven generator 19 is mounted in the trailer to provide electrical power. A hydraulic supply system mounted in the trailer 10 is pressurized by an electric motor 20 to provide hydraulic fluid under pressure for operating the hydraulically powered components described below. The particular drive motors and connecting drive mechanisms are conventional in the art, and therefore are not shown or described in detail. A control panel 21 may be mounted inside the trailer 10, or other convenient location to allow the operator to start and control the operation of the various components in the processing system.

Referring additionally to FIGS. 2 and 3, a hydraulic lift assembly 22 mounted on the rear end of the trailer 10 has a lift carriage 23 mounted on a pair of rails 24. The lift carriage 23 has a rotary actuator 25 at its top end and a sprocket assembly including a pair of laterally spaced drive sprockets 26A connected by a drive shaft 26B driven by a brake motor 27 and upper and lower pairs of laterally spaced idler sprockets 28A, each pair connected by a drive shaft 28B. The sprocket assembly is connected by chains (not shown) with upper and lower pairs of laterally spaced rollers 29 engaged on the rails 24. As seen in FIG. 1, the lift carriage 23 is connected to a platform 30 which has a hydraulic grip member 30A that receives and grips a cart C which contains one or more bags of waste material to be processed. The hydraulic lift assembly 22 raises and lowers the cart and when it reaches its uppermost position at the top end of the rails, the rotary actuator 25 rotates the platform to tip it over and dump out the bags of waste material contained in the cart. The lift assembly eliminates jolting when the cart is raised and pivoted to dump the contents.

Preferably, the poundage of the waste material to be processed is determined after subtracting the weight of the cart. This data is fed into a computer database (not shown) and is used to calculate the proper amount of disinfectant to be used in the process.

Referring again to FIG. 1, the top end of a hopper 31 extends through an opening in the top wall 17 of the trailer at the rear end of the trailer 10 adjacent to the upper end of the hydraulic lift assembly 22 to receive the bags of waste material as they are dumped out of the cart. A modified grinding/grating machine 32 is connected to the bottom end of the hopper 32. A first spray nozzle 38A is mounted above the grinding/grating assembly 32.

Figure 4:
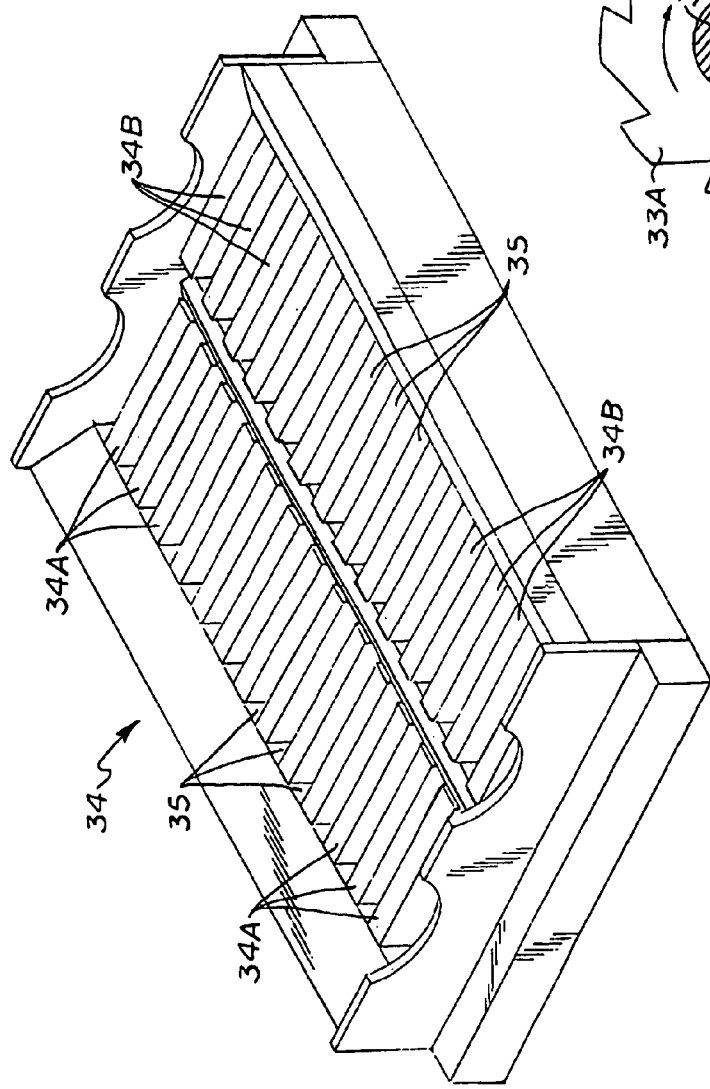
FIG. 4 is an isometric view of a slotted grating plate that is used in the modified grinding/grating machine of the apparatus, shown with the cutting blade elements removed.
Figure 5:
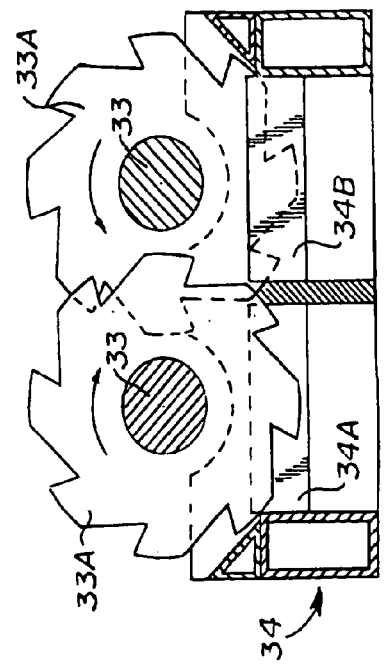
FIG. 5 is a transverse cross sectional view through the slotted grating plate, shown with the cutting blade elements installed.

Referring additionally to FIGS. 4 and 5, the modified grinding/grating machine 32 has a pair of counter-rotating shafts 33 with a plurality of cutter blades or blade knives 33A along the length of the shafts, and is provided with a special grating plate 34 in which the blade knives rotate. The grating plate 34 is a rectangular member having a first and second series of transverse, parallel spaced, rectangular steel bars 34A and 34B defining a series of rectangular slots 35 between each of the bars. The first series of bars 34A are offset from the second series of bars 34B in longitudinal relation. In the modified grinding/grating machine 32, the lower portion of the blade knives 33A extend partially into the slots 35 and rotate against the sides of the slots to grate the materials into particles of from about ⅛" to about ½" in size. The modified grinding/grating machine 32 is preferably powered by an electric motor 36 to rotate the blade knives. The slotted grid plate and cutter blade arrangement of the modified grinder/grater effectively shreds and disintegrates the plastic material of the "red bag" that contains infectious medical waste and overcomes the problem of sticking and gumming caused by the bag material.

Referring again to FIG. 1 a hinged plate 37 mounted in the hopper 31 is pivoted downwardly into the hopper periodically by a hydraulic ram 37A, for example every 10 seconds, to press the materials down and facilitate engagement of the waste material with the rotating blade knives and grating plate of the modified grinding/grating machine 28.

An enclosed upwardly inclined screw conveyor 38 has a lower end disposed beneath the outlet of the modified grinding/grating machine 32 and is joined thereto by a shroud 39 to receive the small particles of waste material. The screw conveyor 38 extends upwardly from the grinding/grating machine 32 at an angle. The lower end of the inclined screw conveyor 38 serves as a vat for holding a quantity of chemical disinfectant in which the particles are immersed as they enter the conveyor and its upper discharge end is adjoined to the lower end of an enclosed tubular high-speed screw conveyor 45, as explained hereinafter. The inclined screw conveyor 38 is preferably powered by hydraulic motor 40 connected to rotate the screw and continuously transport the particles away from the grinding/grating machine 32.

As shown in FIG. 1, the hopper 31, the grinding and grating machine 32, the shroud 39, the inclined screw conveyor 38, and the vertical screw conveyor 45 are all joined together to form an enclosed system.

A pair of laterally opposed second spray nozzles 38B are mounted directly under the grinding/grating assembly 32 adjacent to the entry point of the vat at the lower end of the inclined screw conveyor 38. The nozzles 38A and 38B are connected through a calibrated mixing and pump system (not shown) to a fresh water tank 41 and a disinfectant tank 42 mounted inside the trailer. The tanks 41 and 42 are preferably formed of poly propylene. The disinfectant tank 42 is filled with a sodium hypochlorite (NaOCl) disinfectant solution adjusted to a pH of about 4.0 to about 6.0 to increase the hypochlorous acid (HOCl) component and significantly increase the microbiocidal activity of the disinfectant. The disinfectant inside the tank 42 may be continuously circulated by a pump (not shown) to insure a homogeneous mixture.

A three-stage HEPA filter 43 and suction fan 44 are connected by a duct 43A to the upper end of the hopper 27 and an exhaust duct connected with the HEPA filter extends through the roof or top wall 17 of the trailer 10. The high-speed blower or suction fan 44 produces a vacuum or negative pressure in the enclosed system of preferably about 15 psi and draws the air in the enclosed system through the HEPA filter 43 and vents it to the atmosphere. The HEPA filter 43 contains a series of filter media which effectively captures and destroys chemical fumes, airborne dust particles, odors, and bacteria and the air discharged from the HEPA filter is safe to the environment and to humans.

The grating plate 34 is heated by the friction of the blade knives 33A rotating at low rpm against the steel bars 34A, 34B, and the blade knives not only reduce the size of the particles of waste material, but also act as fan blades to force the hot air generated by the heated grating plate through the particles to partially dry the particles. The HEPA filter 40 effectively captures and destroys chemical fumes, airborne dust particles, odors, and bacteria that may be present during and after the grinding and grating operation. The product leaving the grinder/grater is a confetti-like material and is unrecognizable as to the source.

As the bags of waste material enter the hopper 32, they are sprayed with the disinfectant solution by the first nozzle 38A. As the small particles of waste material leave the grinding/grating machine 28, the particles are once again sprayed with another application of the disinfectant solution by the second nozzles 38B disposed beneath the grinding/grating machine, and drop into the lower end of the inclined screw conveyor 38 and become immersed in the disinfectant solution contained in the lower end of the conveyor, which serves as a vat. As the previously immersed particles travel upward in the conveyor 38, they become thoroughly mixed and saturated with the disinfectant solution, and after traveling a distance in the conveyor, the excess disinfectant drains down the inclined conveyor and is contained in its lower end.

Drying is accomplished by industrial heaters connected in communication with the enclosed system to dry the waste material with hot air. Alternatively, as indicated by dashed line in FIGS. 1 and 6, the exhaust of the engine of the diesel driven generator 19 may be connected in communication with the enclosed system to facilitate drying, whereby the waste material is subjected to the hot exhaust of the generator engine during the steps of grinding, grating, macerating, spraying, immersing and conveying in the enclosed system, and the confetti-like waste material becomes dried as it reaches the discharge end of the inclined screw conveyor.

As stated above, the discharge end of the inclined conveyor 38 is connected to the lower end of the enclosed tubular high-speed vertical conveyor 45. The preferred vertical conveyor 45 is powered by a hydraulic motor 46 connected to rotate the screw and swirl the dried confetti-like material in a spiral as it is transported vertically upward. The vertical conveyor 45 is made in two tubular sections. The tubular upper section 45A of the vertical conveyor 45 extends through the top wall 17 of the trailer 10 and is rotatably connected with the tubular lower section 45B to rotate about the common vertical axis. A rotary seal (not shown) may be provided in the top wall 17 of the trailer 10 through which the upper section 45A of the vertical conveyor passes.

The inlet end of an elongate enclosed tubular discharge screw conveyor 47 is connected by a rotatable connection 48 to the upper end 45A of the vertical conveyor 45. The preferred discharge conveyor 47 is powered by a hydraulic motor 49 connected to rotate the screw at about 120 rpm. In some applications, one or more hydraulic cylinders may be connected between the upper end of the vertical conveyor 45 and the tubular discharge conveyor 47 to pivot the discharge conveyor in a horizontal and/or vertical plane.

After reaching the upper end of the vertical conveyor 45, the dried confetti-like material enters the discharge conveyor 47 and is discharged through the outlet 50 at the outer end of the discharge conveyor. The discharge conveyor 47 can rotate 360° about a vertical axis relative to the trailer and pivot upwardly or downwardly to facilitate discharging the confetti-like material into a convenient receptacle, such as a dumpster, compactor, or dump truck.

FIG. 1 shows schematically, in dashed line, a modification of the trailer 10 wherein a compactor 51 is mounted in or on the trailer chassis, and the dried confetti-like material is discharged through the outlet 50 at the outer end of the discharge conveyor 47 into the compactor. It should be understood that the processing apparatus 18 may also be mounted on a skid which is transported and placed at a location.

OPERATION

Figure 6:
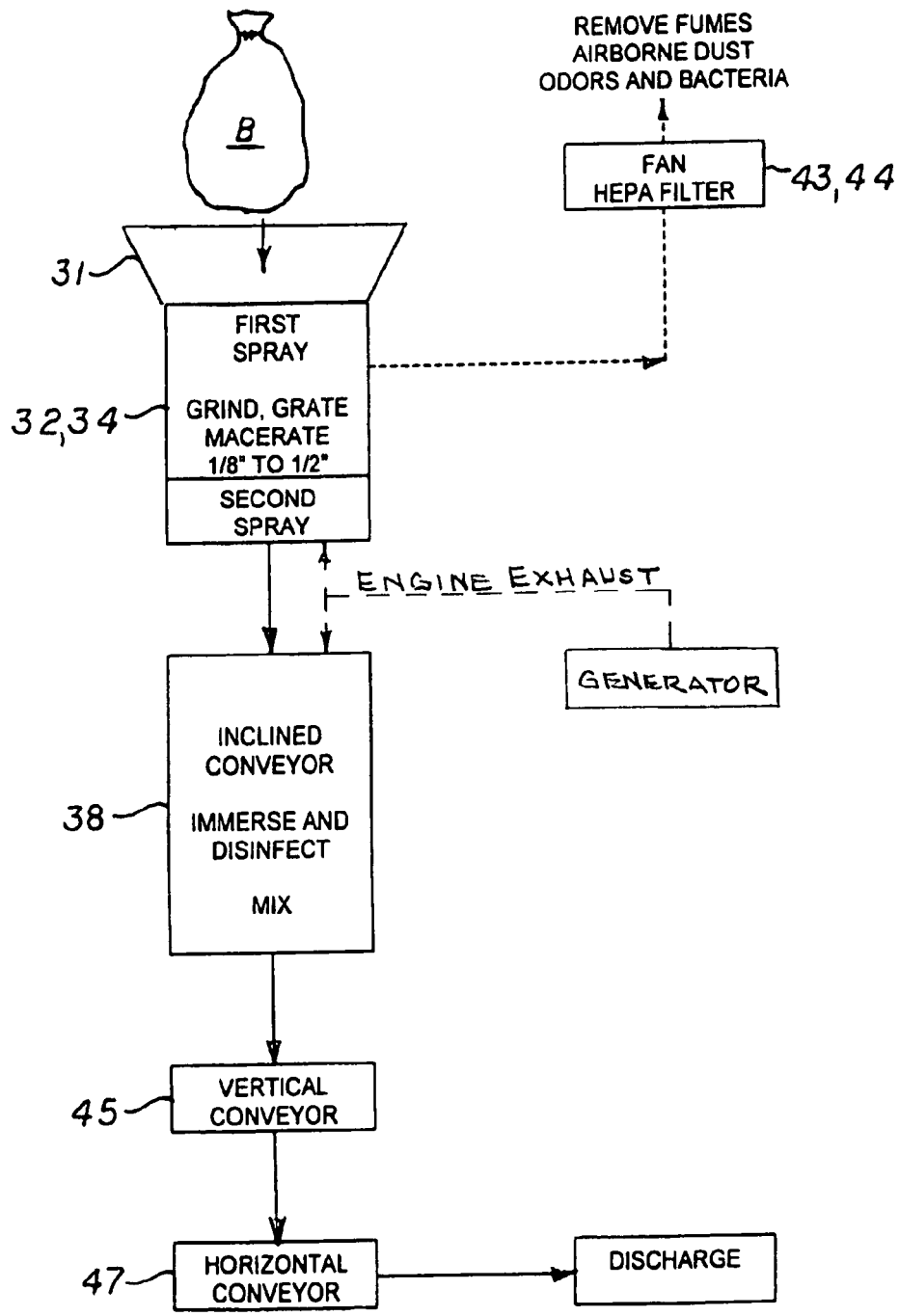
FIG. 6 is a flow diagram illustrating the steps in the process for grinding, grating, macerating and chemically disinfecting waste materials in accordance with the present invention.

Referring now to FIGS. 1 and 6, the mobile trailer and apparatus is transported to a health care facility. The outlet end 50 of the discharge conveyor 47 is positioned over a suitable receptacle, such as a dumpster, compactor, or dump truck. The bags B of infectious medical waste are loaded into carts C. After the weight of the bags of waste material has been determined and recorded, the amount and pH level of the sodium hypochlorite (NaOCl) disinfectant solution is adjusted to a pH of about 4.0 to about 6.0 to produce a final concentration of 2,500 ppm hypochlorous acid (HOCl). The hypochlorous acid serves as the microbiocidal component of the disinfectant solution. At this pH range, the hypochlorite ion (OCl) decreases and concentration of hypochlorous acid (HOCl) increases and thus, the microbiocidal activity of the sodium hypochlorite (NaOCl) solution increases. The speed of the conveyors is adjusted to provide a mixing time corresponding to the type and volume of material to be processed.

The bags B of infectious medical waste material are dumped into the hopper 31 and fed into the modified grinding/grating machine 32, while they are sprayed with the disinfectant solution by the first nozzle 38A. The modified grinding/grating machine 32 of the present invention is distinguished over conventional shredders used in other systems in that conventional shredders cut, slice, or tear the materials into small pieces, whereas the modified grinding/grating machine 32 not only cuts and grinds the bags of waste material, but also grates the materials against the rectangular bars of the grating plate to grate and macerate the materials into particles of from ⅛" to ½" in size.

The blade knives 33A not only further reduce the size of the particles of waste material, but also force hot air from the heated grating plate 34 through the particles to partially dry the particles.

The suction fan 44 and HEPA filter 43 effectively captures and destroys chemical fumes, airborne dust particles, odors, and bacteria which may be present during and after the grinding and grating operation.

As the small particles of waste material leave the grinding/grating machine 28, the particles are once again sprayed with another application of the disinfectant solution by the second nozzles 38B disposed beneath the grinding/grating machine, and drop into the lower end of the inclined screw conveyor 38.

The grated particles of waste material drop into the lower end of the inclined screw conveyor 38 and become immersed in the disinfectant solution contained in the lower end of the conveyor. As the previously immersed particles are rotated and travel upward in the conveyor 38, they become thoroughly mixed and saturated with the disinfectant solution, and after traveling a predetermined distance in the conveyor, excess disinfectant drains down the inclined conveyor 38 and is contained in its lower end which serves as the vat. In the present system, there is no drain that allows the chemical to escape onto the ground. The chemical volume is controlled by the amount (weight) of the waste material being processed. The particles are dried as they reach the discharge end of the inclined screw conveyor.

As described previously, drying is accomplished by industrial heaters connected in communication with the enclosed system to dry the waste material with hot air. Alternatively, as indicated by dashed line in FIGS. 1 and 6, the exhaust of the engine of the diesel driven generator 19 may be connected in communication with the enclosed system to facilitate dr in during the steps of grinding, grating, maceratin in immersing and conveying. Also as described previously, the high-speed blower or suction fan 44 of the HEPA filter 43 connected by the duct 43A to the hopper 27 above the grinding/grating machine 32 produces a vacuum or negative pressure in the enclosed system and draws the air in the enclosed system through the HEPA filter 43 and vents it to the atmosphere. Thus, drying is further facilitated by the vacuum or negative pressure produced by the suction fan 44 of the HEPA filter 43, since the adjoined hopper 31. the grinding/grating machine 32, the shroud 39, and conveyors 38 and 45 are an enclosed system.

The dry confetti-like material enters into the vertical screw conveyor 45. The vertical screw conveyor 45 swirls the dried confetti-like material in a spiral as it is transported vertically upward.

The dried confetti-like material enters the elongate tubular discharge screw conveyor 47 and is discharged through the discharge outlet 50 into a receptacle, such as a dumpster, compactor, or dump truck. It can then be safely transported to a landfill along with general waste from the health care facility. The resulting product is a dry, fluffy, confetti-like material that is unrecognizable as to the source.

Tests have shown that the present process using a sodium hypochlorite (NaOCl) disinfectant solution adjusted to a pH of about 4.0 to about 6.0 and final concentration of 2,500 ppm hypochlorous acid will produce at least a 4 $\log_{10}$ reduction or 99.99%, and in most cases, a 6 $\log_{10}$ reduction or 99.9999% reduction in the numbers of active microorganisms. The present system can also process from 1,500 to 3,000 pounds of waste per hour.

While this invention has been described fully and completely with special emphasis upon preferred embodiments, it should be understood that within the scope of the appended claims the invention may be practiced otherwise than as specifically described herein.

We claim:

1. A method for processing and chemically disinfecting infectious waste material, comprising the steps of:

transporting a wheeled enclosure containing lift and dumping means, a hopper, grinding and grating means, immersion vat means, conveyor means, suction and filter means, an electrical generator driven by a petroleum fuel engine, a source of chemical disinfectant, and a source of fresh water, to a location where infectious waste material is stored;

said petroleum fuel engine having an exhaust connected in communication with said grinding and grating means, said immersion vat means, and said conveyor means;

placing said infectious waste material into a cart, placing said cart on said lift and dumping means, and dumping said infectious waste material into said hopper;

feeding said infectious waste material from said hopper to said grinding and grating means and grinding, grating, and macerating it into waste particles of a small size range of confetti-like material which is unrecognizable as to the source;

spraying said infectious waste material with a chemical disinfectant as it is fed to said grinding and grating means and again after grinding, grating, and macerating it;

immersing said waste particle material in said chemical disinfectant contained in said immersion vat means;

after immersion, conveying said waste particle material from said vat means to the exterior of said wheeled enclosure in said conveyor means and mixing said waste particles and said chemical disinfectant together as they are conveyed therein;

conducting the exhaust of said petroleum fuel engine into said grinding and grating means, said immersion vat means, and said conveyor means whereby said waste particle material is heated during said steps of grinding, grating, macerating, spraying, immersing and conveying and becomes dried prior to being conveyed to the exterior of said wheeled enclosure by said conveyor means;

subjecting said grinding and grating means, and said conveyor means to negative air pressure as said particles are being ground, grated, macerated, and conveyed, and venting the air through a filter to remove chemical fumes, airborne dust particles, odors, and bacteria therefrom; and discharging said dry confetti-like material from said enclosed screw conveyor system.

2. The method according to claim 1, wherein said steps of spraying and immersing said waste particles in a chemical disinfectant comprises immersing said waste particles in a liquid solution of sodium hypochlorite (NaOCl) containing an effective concentration of hypochlorous acid (HOCl) sufficient to produce at least a 4 $\text{Log}_{10}$ reduction in the numbers of active microorganisms present in said waste particles.

3. The method according to claim 1, wherein said steps of spraying and of immersing said waste particles in a chemical disinfectant comprises immersing said waste particles in a liquid solution of sodium hypochlorite (NaOCl) adjusted to a pH in the range of about 4.0 to about 6.0 to produce a final concentration of 2,500 ppm hypochlorous acid (HOCi) which serves as the microbiocidal component of said disinfectant solution.

4. The method according to claim 1, wherein said step of grinding grinding, grating, and macerating said waste particles in said grinding and grating means includes passing said waste material through a set of blades rotatably engaged in slots in a slotted grate to grind, grate, macerate, and reduce said waste material into confetti-like particles which are unrecognizable as to the source.

5. The method according to claim 1, including the further step of compacting said dry confetti-like material discharged from said conveyor means.

6. A mobile self-contained waste processing and chemical disinfecting apparatus for processing infectious waste material comprising:

a wheeled enclosure transportable to a predetermined location and containing an electrical generator driven by a petroleum fuel engine, a source of chemical disinfectant and a source of fresh water;

lift and dumping means on said wheeled enclosure for receiving a cart containing infectious waste material and dumping said infectious waste material from said cart;

a hopper in said wheeled enclosure adjacent to said lift and dumping means for receiving said dumped infectious waste material;

grinding and grating means in said wheeled enclosure connected to said hopper for receiving said infectious waste material and grinding, grating, and macerating it into waste particles of confetti-like material which is unrecognizable as to the source;

first spray means connected with said hopper and with said chemical disinfectant source for wetting said infectious waste material as it is received in said grinding and grating means, an enclosed upwardly inclined screw conveyor connected with said grinding and grating means for receiving said waste particle material therefrom and containing a quantity of chemical disinfectant at a lower end thereof for receiving said waste particle material, immersing it in said chemical disinfectant, and conveying said waste particle material to an upper end;

second spray means disposed between said grinding and grating means and said lower end of said upwardly inclined screw conveyor and connected with said chemical disinfectant source for wetting said waste particle material as it is received in said upwardly inclined screw conveyor;

an enclosed vertical screw conveyor having a lower portion disposed within said wheeled enclosure connected with said inclined enclosed screw conveyor upper end for receiving said waste particle material therefrom and an upper portion extending outwardly through said wheeled enclosure;

said petroleum fuel engine having an exhaust connected in communication with said grinding and grating means, said upwardly inclined screw conveyor, and said vertical screw conveyor for heating the waste particle material during the steps of grinding, grating, macerating, spraying, immersing and conveying such that it becomes dried as it reaches said upper end of said inclined screw conveyor;

suction and filter means connected in communication with said grinding and grating means, said upwardly inclined screw conveyor, and said vertical screw conveyor to produce a negative pressure therein to remove chemical fumes, airborne dust particles, odors, and bacteria therefrom; and an enclosed horizontal discharge screw conveyor disposed exterior of said wheeled enclosure connected a first end with said vertical enclosed screw conveyor outwardly extending portion for receiving said waste particle material therefrom and having a discharge outlet at a second end for discharging it.

7. The apparatus according to claim 6, wherein said chemical disinfectant comprises a liquid solution of sodium hypochlorite (NaOCl) containing an effective concentration of hypochlorous acid (HOCi) sufficient to produce at least a 4 $Log_{10}$ reduction in the numbers of active microorganisms present in said waste particles.

8. The apparatus according to claim 6, wherein said chemical disinfectant comprises a liquid solution of sodium hypochiorite (NaOCl) adjusted to a pH in the range of about 4.0 to about 6.0 to produce a final concentration of 2,500 ppm hypochlorous acid (HOCl) which serves as the microbiocidal component of said disinfectant solution.

9. The apparatus according to claim 6, wherein said grinding and grating means has a slotted grate and a set of blades rotatably engaged therein for receiving said infectious waste material, and grinding, grating, macerating, and reducing it into confetti-like particles of from about ⅛" to about ½" in size.

10. The apparatus according to claim 6, further comprising:
compactor means for receiving and compacting said discharged waste particle material.

11. The apparatus according to claim 6, wherein said lift and dumping means comprises a pair of rails mounted on the rear end of said trailer;
a lift carriage having rollers engaged with said pair of rails, a chain and sprocket assembly connected with said rollers, and a hydraulic brake motor connected with said chain and sprocket assembly for raising and lowering said carriage on said rails, and a rotary actuator at an upper end of said carriage; and
a platform connected with said rotary actuator for supporting a cart containing one or more bags of waste material to be processed and having hydraulic grip means for gripping the cart;
said rotary actuator rotating said platform and tipping the cart over as said carriage reaches an uppermost position to dump the contents of the cart into said hopper.

* * * * *